United States Patent [19]

Lohman

[11] Patent Number: 5,137,318
[45] Date of Patent: Aug. 11, 1992

[54] SUPPORT MEANS FOR A GRIPPING DEVICE

[76] Inventor: Oskar R. Lohman, Smedjevaegen 16, S-131 33 Nacka, Sweden

[21] Appl. No.: 674,379
[22] PCT Filed: Oct. 25, 1989
[86] PCT No.: PCT/SE89/00593
§ 371 Date: Apr. 15, 1991
§ 102(e) Date: Apr. 15, 1991
[87] PCT Pub. No.: WO90/04361
PCT Pub. Date: May 3, 1990

[30] Foreign Application Priority Data

Oct. 25, 1988 [SE] Sweden .................. 8803813

[51] Int. Cl.⁵ .................................... A01M 3/00
[52] U.S. Cl. .......................... 294/100; 294/99.2
[58] Field of Search ............... 294/99.2, 100; 248/176

[56] References Cited

U.S. PATENT DOCUMENTS

| | | | |
|---|---|---|---|
| 1,011,597 | 12/1911 | Fischler | 294/99.2 X |
| 1,284,060 | 11/1918 | Colman | 294/99.2 |
| 4,033,350 | 5/1977 | Hoshi . | |
| 4,078,569 | 3/1978 | Hoshi . | |
| 4,304,398 | 12/1981 | Crowell | 294/95 X |
| 4,442,837 | 4/1984 | Keatley . | |
| 4,768,288 | 9/1988 | Culbertson | 294/99.2 X |
| 4,802,703 | 2/1989 | Gabel | 294/99.2 |
| 5,002,323 | 3/1991 | Idsund | 294/100 |

FOREIGN PATENT DOCUMENTS 378116 6/1985 Austria .
1001665 2/1952 France .
2313885 1/1977 France .

Primary Examiner—Margaret A. Focarino
Assistant Examiner—Joseph D. Pape
Attorney, Agent, or Firm—Beveridge, DeGrandi & Weilacher

[57] ABSTRACT

An assembly which includes supporting structure for a gripping device such as a pair of tweezers. The support structure includes a cylindrical member for rotational support of the tweezer legs relative to a cross-piece which carries a support leg. The support leg extends substantially in parallel with the tweezer legs, and is provided with a support foot for contact with the work piece. At its rear end, the support leg is adjustably connected to the cross-piece. A retention device maintained the tweezer legs at a specific location along the axial axis during operation. A maneuver sleeve surrounds and is displaceably guided along the tweezer gripping legs for accomplishing compression and opening, respectively, of the tweezer legs upon longitudinal movement. Preferably, a maneuver rod extends along the central axis through a hollow cylindrical portion defining the base or stem of the tweezer legs. The maneuver rod is connected to the maneuver sleeve by, for example, a pin extending between the tweezer legs. By forcing the maneuver rod downwardly, the attached maneuver sleeve slides over the legs so as to compress inwardly the outwardly diverging legs. The retention device acts to maintain the tips of the tweezer legs to a position between the maneuver sleeve and the support foot so as to help avoid piercing of a person or animal's skin.

15 Claims, 2 Drawing Sheets

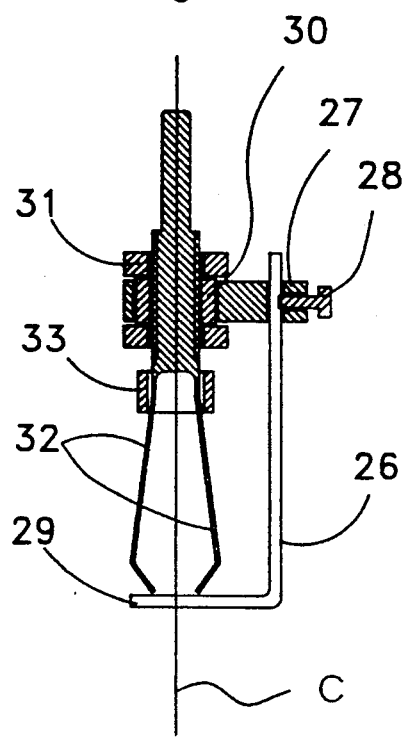
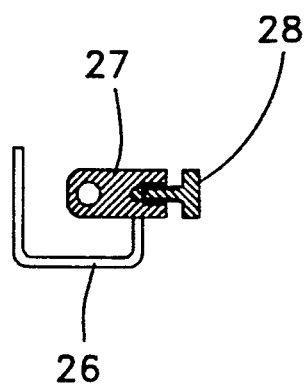
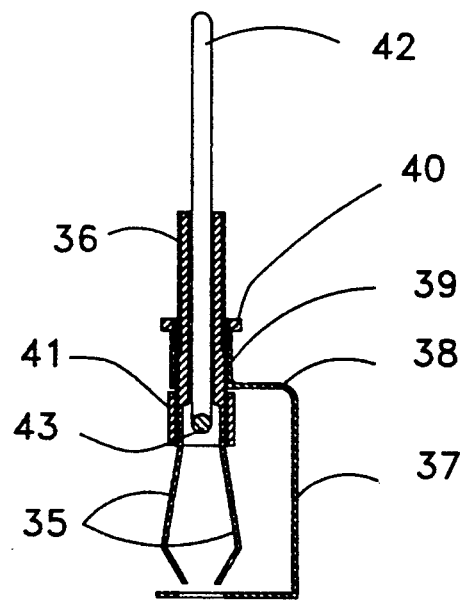

SUPPORT MEANS FOR A GRIPPING DEVICE

This invention concerns a support means for a pair of tweezers or like gripping devices comprising one or more support legs associated with the tweezers or gripping means, which support leg or legs are intended to stabilize and support the tweezers for a more precise handling of the latters when picking objects and to enable rotation of the picked objects while maintaining support.

Previously known tweezers or like gripping means lack such a support means, and for elderly people with a bit shaky hands who have difficulty in holding the tweezers steady in a correct position there is a problem, for example, in removing a splinter from a wound without hurting themselves with the tweezers tips.

Also for surgical and veterinary purposes, tweezers and other like gripping devices are difficult to handle with precision, and in electronic industry mounting of chips and other small size components demands a very precise handling of tweezers.

A specific application for tweezers is within the veterinary field, namely for removal of ticks from animals like dogs and cats. Ticks are removed by gripping and rotation. It is not until a tick has been rotated about one and a half revolutions that it will lose its grip such that it can be lifted away. If not rotated, there is a risk the head of the tick is left when a lifting force is applied on the tick. This increases the risk for infections on the treated animal. Performing a combined gripping and rotating movement with a prior art pair of tweezers is very difficult or almost impossible. Usually the handling of the tweezers has to be performed with one hand only since the other hand is occupied holding the dog or cat.

The main purpose of the invention is to accomplish a support means for a gripping device, such as a pair of tweezers, by which a stabilizing support of the tweezers relative to the working object is obtained for facilitating gripping, locating or removal of objects, and which enables rotation of the objects with the stabilizing support maintained.

Preferred embodiments of the invention are below described in detail with reference to the accompanying drawings.

In the drawings:

FIG. 5 shows a side view of a pair of tweezers according to still another embodiment of the invention.

FIG. 6 shows an end view of the tweezers in FIG. 5.

FIG. 7 shows a side view partly in section, of a pair of tweezers provided with a support means according to a further embodiment of the invention.

Figure 1:
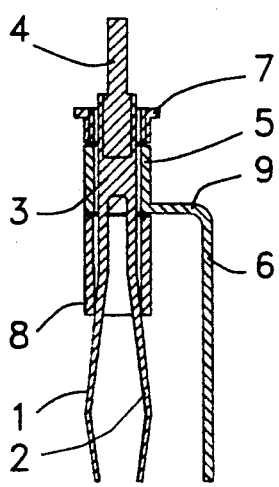
FIG. 1 shows a side view, partly in section, of a pair of tweezers provided with a support device according to the invention.

The tweezers shown in FIG. 1 comprises two legs 1, 2 which are formed as a common portion in the shape of a cylindrical common member or spindle 3. At its rear end, this spindle has an outer thread and is provided with an extension 4 with a smaller diameter. A support leg 6 is connected to the spindle 3 via a cross piece 9 and a sleeve 5 for enabling rotation as well as axial displacement. On the thread of the spindle 3, there is mounted a nut 7 formed of, for instance, a fiber material for increased friction. This nut 7 acts as an axial stop for the sleeve 5. Accordingly, the axial stop is adjustable and enables the axial position of the sleeve 5 and the support leg 6 to be varied.

Around the rear ends of the tweezers legs 1, 2, there is mounted a sleeve 8 which is displaceable along the legs 1, 2. Since the rear ends of the legs 1, 2 diverge in the forward direction, a forward directed movement of the sleeve 8 accomplishes a compression of the legs 1, 2. At retraction of the sleeve 8 to the position illustrated in FIG. 1, the tweezer legs open due to the elastic forces stored in the material as in conventional tweezers. The tweezers may consist of metal or plastics. To bring down the manufacturing costs, the tweezers and the sleeve 8 may be formed by injection moulded plastics.

Figure 2:
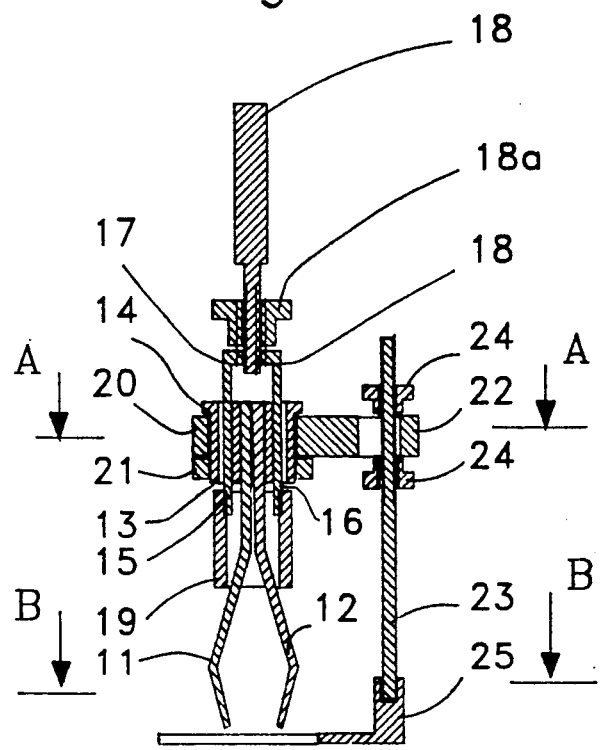
FIG. 2 shows a side view of a pair of tweezers according to another embodiment of the invention.
Figure 4:
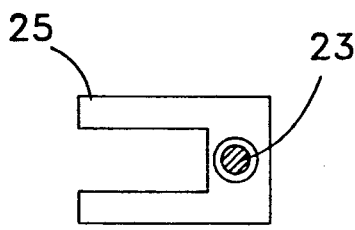
FIG. 4 shows a cross section along line B—B in FIG. 2.
Figure 3:
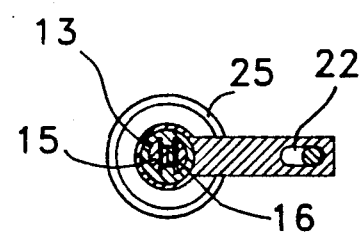
FIG. 3 shows a cross section along line A—A in FIG. 2 with a modified support base.

In FIGS. 2 and 3, there is shown a pair of tweezers provided with a support means according to the invention in and which the tweezers comprise two legs 11, 12 which are joined at their top ends by mounting in a cylindrical member 13 so as to define a common portion in the region of contact between the top ends of legs 11, 12. The latter is formed with a collar 14 and two axially directed and each other opposed grooves on the member 13. In these grooves there are received two legs 15, 16 which are axially displaceable relative to the cylindrical member 13 and which integral with a spindle 17. The latter has a threaded axial bore for cooperation with an adjustment screw 18. A nut 18a is employed to lock the screw 18 relative to the spindle 17. The legs 15, 16 are locked against radial outward movement by a sleeve 19. The cylindrical member 13 is rotatively journalled in a bore in a cross member 20 and is axially locked between the collar 14 and a lock ring 21 mounted in a peripheral groove on the cylindrical member 13. The cross member 20 has a transverse rectangular aperture 22 adapted to receive a support leg 23. The latter has a threaded upper end engaged by two nuts 24 for enabling longitudinal as well as lateral adjustment. At its lower end, the support leg 23 is provided with a foot 25. The design of the latter appears in FIG. 4. FIG. 3 illustrates a modified base 25' which is circular in shape.

The above described support means is particularly suitable for a one-hand operation, for instance at removal of ticks from a dog or cat. The adjustment screw 18 is grasped between your thumb and forefinger to locate the support foot 25 on the dog or cat's skin in such a way that the tick to be removed falls between the tweezers legs 11, 12. Thereafter, the screw 18 is forced downwards to make the legs 15, 16 move along the tweezers legs 11, 12, whereby the latters, due to their diverging upper parts, are forced together grasping the tick. When the tweezer legs are secured to the tick, the screw 18 is rotated as is the spindle 17, the legs 15, 16, the cylindrical member 13 and the legs 11, 12. The tick is rotated and forced to let go from the dog or cat's skin. This rotation may be carried out without moving your finger and thumb from the screw 18, and because of the fact that the diameter of the screw 18 is small it may be rotated several full revolutions. Finally, the tweezers and the support leg are lifted away from dog or cat together with the tick. The downward movement of the screw 18 is limited by the abutment of the lower end screw 18 against the cylindrical member 13, and since the length of the downward movement of the screw 18 determines the compression force exerted on the legs 11, 12 by the sleeve 19, the setting of screw 18 is decisive for the gripping force executed on the tick.

In FIGS. 5 and 6, there is shown a third embodiment of the invention wherein a support leg 26 is adjustably secured to a cross piece 27 by means of a lock screw 28. The support leg is bent in a right angle at its lower end to form a support foot 29. In parallel with the support leg 26, the tweezer pair is rotatively journalled in the cross piece 27 via a sleeve 30. As shown in FIG. 5, tweezer legs 32 come together to form a common portion which extends through sleeve 30. Central axis C represents the central axis of the common portion. The latter is axially locked relative to the cross piece 27 by means of a nut 31, and around the upper parts of the tweezer legs 32 there is a maneuver sleeve 33 for actuating the tweezer legs as in the above described embodiments.

In FIG. 7, there is shown a fourth embodiment of the invention wherein two legs 35 are formed in one piece with a common cylindrical portion 36, which at its upper end comprises an external thread. A support leg 37 is rotatively jounalled as well as axially displaceable relative to the portion 36 by means of a cross piece 38 and a sleeve 39. A nut 40, preferably of a fiber material for increased friction, engages the thread on the portion 36, thereby serving as an axial stop for the sleeve 39 and the support leg 37. Around the legs 35, there is maneuver sleeve 41 for actuating the legs 35 when longitudinally moved along the latters by means of a maneuver rod 42 extending through an axial bore in the cylindrical portion 36. The maneuver rod 42 is coupled to the sleeve 41 by means of a transverse pin 43. Due to the diverging upper parts of the legs 35, a downward movement of the maneuver sleeve 41 causes a compression of the legs 35, At retraction of the sleeve 41 to the position illustrated in FIG. 7, the tweezer legs 35 are opened.

It is to be understood that the support member, although described above and shown in the drawing figures as a single leg, as well may comprise two or more legs.

What is claimed is:

1. Support means for a gripping device having compressible gripping legs each supported at a rear end by a common portion, comprising:
   a support member which includes a support leg extending substantially parallel with a central axis of the common portion;
   means for axially locking the common portion in a position along the central axis;
   said support means including journal means for retaining the common portion such that the common portion is rotatively journalled relative to said support member; and
   compression means for compressing the compressible gripping legs of the gripping device, said compression means being dimensioned and arranged for axial adjustment along the central axis.

2. Support means according to claim 1, wherein said support member includes a cross-piece extending away from said support leg, and said journal means including an aperture formed in a first end of said cross-piece which is spaced from said support leg.

3. Support means according to claim 2, wherein said means for axially locking includes adjusting means for adjustably positioning the common member with respect to said cross-piece.

4. Support means according to claim 3, wherein said locking means includes a nut threadably engageable with the common portion and in abutting contact with said cross-piece.

5. Support means according to claim 2, wherein said journal means further comprises a sleeve member with a hollow interior which is dimensioned to rotatively receive the common portion, and said sleeve member is connected with said first end of said cross-piece.

6. Support means according to claim 1, wherein said compression means comprises a maneuver sleeve surrounding the gripping legs and dimensioned and arranged for axial displacement with respect to said gripping legs such that a divergent portion of said gripping legs is compressed inwardly when said maneuver sleeve travels over said divergent portion and is released outwardly when said maneuver sleeve is shifted from contact with said divergent portion.

7. Support means according to claim 1, wherein said means for axially locking the common portion includes a member positioned above said journal means and in contact with said journal means so as to prevent axial downward displacement of the common portion.

8. Support means according to claim 1, wherein said compression means includes a rod telescopically displaceable with respect to the common portion.

9. Support means according to claim 1, wherein said compression means includes an elongated rod slideably retained within an elongated through-hole centrally formed in the common portion, said elongated rod being of a length greater than the elongated through-hole formed in the common portion such that the ends of said elongated rod are spaced apart so as to be positioned to opposite ends of the elongated through-hole formed in the common portion.

10. Support means according to claim 1, wherein said compression means includes a rod slideably displaceable within a through-hole formed in the common portion, and said compression means includes a maneuver sleeve and means for attaching said maneuver sleeve to said rod such that displacement of said rod results in displacement of said maneuver sleeve, and said maneuver sleeve being dimensioned and arranged so as to compress inwardly a divergent segment of the compressible gripping legs.

11. Support means according to claim 10, wherein said means for attaching said maneuver sleeve to said rod includes a pin member extending in between the gripping legs.

12. Support means for a gripping device having compressible gripping legs with each gripping leg having a forward end and a rear end with the rear end extending into a common portion, and each gripping leg extending into a common portion, and each gripping leg extending essentially along in the direction of a central axis of said gripping device, comprising:
   a support member which includes a support leg extending substantially parallel with the central axis of the gripping device;
   axial retention means for axially locking the common portion in a position along the central axis and for retaining the common portion such that the common portion is rotatable relative to said support member; and
   a compression device axially displaceable with respect to said retention means and in contact with the gripping legs for compressing the compressible gripping legs closer together.

13. Support means as recited in claim 12, wherein said support means includes an end support foot and wherein said retention means limits a position of the forward ends of said gripping legs to a position which is between said compression device and the end support foot.

14. Support means according to claim 12, wherein said compression device includes a maneuver rod axially slideable within the common portion of the gripping device, a maneuver sleeve surrounding the gripping legs and attachment means for attaching said maneuver sleeve to said maneuver rod.

15. Support means according to claim 14, wherein said attachment means includes a pin diametrically extending within and fixed to the maneuver sleeve and said pin being secured to one end of said maneuver rod and extending between the gripping legs.

* * * * *